United States Patent [19]

Thompson et al.

[11] 4,122,081

[45] Oct. 24, 1978

[54] 5′-HYDROXYLEUROSINE AND RELATED COMPOUNDS

[75] Inventors: Gerald L. Thompson; Gloria C. Paschal; Robert A. Conrad, all of Indianapolis, Ind.

[73] Assignee: Eli Lilly and Company, Indianapolis, Ind.

[21] Appl. No.: 822,466

[22] Filed: Aug. 8, 1977

[51] Int. Cl.$^2$ ............................................. C07D 519/04
[52] U.S. Cl. ................................... 260/287 B; 424/258
[58] Field of Search ....................................... 260/287 B

[56] References Cited

U.S. PATENT DOCUMENTS 3,370,057   4/1964   Svoboda et al. ..................... 424/258

OTHER PUBLICATIONS

Kutney et al., Heterocycles, 4, 1377 (1976).

*Primary Examiner*—Donald G. Daus
*Assistant Examiner*—David E. Wheeler
*Attorney, Agent, or Firm*—James L. Rowe; Arthur R. Whale

[57] ABSTRACT

5′-Hydroxyleurosine, 5′-hydroxyleuoformine and related compounds, useful in inhibiting the growth of experimental tumors.

5 Claims, No Drawings

5'-HYDROXYLEUROSINE AND RELATED COMPOUNDS

BACKGROUND OF THE INVENTION

The vinca alkaloids, a group of dimeric indole dihydroindoles, have achieved considerable prominence as marketed or experimental chemotherapeutic agents for the treatment of susceptible carcinomas, sarcomas, and leukemias. These agents are used both alone and in combination with other chemotherapeutic agents. As a class, the vinca alkaloids include compounds obtainable from the leaves of Vinca rosea, derivatives produced by chemical modification thereof and more recently, dimeric alkaloids produced by coupling two "monomeric" indoles via a modified Polonovski reaction—see Langlois and Potier, Tetrahedron Letters, 1099 (1076), Potier, et al., J.C.S. Chem. Comm., 670 (1975), Kutney et al., Heterocycles, 3, 205 (1975) and Atta-ur-Rahman Tetrahedron Letters, 2351 (1976).

A majority of the vinca alkaloids can be described by the following formula:

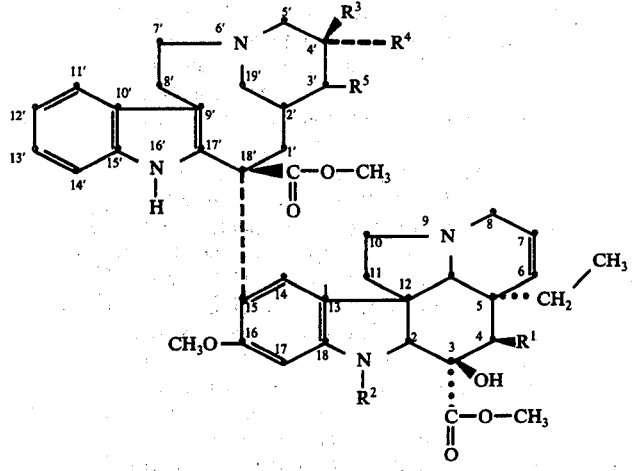

I

In the above formula where $R^1$ is acetoxy, $R^2$ is methyl, $R^3$ is hydroxyl, $R^4$ is ethyl and $R^5$ is H, VLB is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" but $R^3$ is ethyl and $R^4$ is hydrogen, deoxy VLB "B" is represented; and where $R^1$ is acetoxy, $R^2$ is methyl, $R^3$ is ethyl and $R^4$ and $R^5$ taken together form an α-epoxide ring, leurosine is represented.

The above-mentioned alkaloids are described in the following publications: leurosine (vinleurosine—U.S. Pat. No. 3,370,057), VLB (vincaleukoblastine, vinblastine— U.S. Pat. No. 3,097,137), leurosidine (vinrosidine) and vincristine (leurocristine or VCR) (both in U.S. Pat. No. 3,205,220), and deoxy VLB "A" and "B", Tetrahedron Letters, 783 (1958). Other alkaloids obtained from vinca rosea include 4-desacetoxy vinblastine (U.S. Pat. No. 3,954,773); 4-desacetoxy-3'-hydroxyvinblastine (U.S. Pat. No. 3,944,554); leurocolombine (2'-hydroxy VLB—U.S. Pat. No. 3,890,325) and vincadioline (3'-hydroxy VLB—U.S. Pat. No. 3,887,565).

Two of the above alkaloids, VLB and vincristine, are now marketed as drugs for the treatment of malignancies, particularly the leukemias and related diseases in humans. Of these marketed compounds, vincristine is a most active and useful agent in the treatment of leukemias but is also the least abundant of the antineoplastic alkaloids of Vinca rosea. Jovanovics et al.—U.S. Pat. No. 3,899,493—have developed an elegant oxidative procedure for converting the more abundant alkaloid VLB to vincristine employing chromic acid in acetone and acetic acid at about −60° C. The same procedure has been used to prepare leuroformine (N-formylleurosine) from leurosine—see Belgian Pat. No. 811,110. Leuroformine has also been found in extracts of leaves of Vinca rosea. This alkaloid is currently undergoing a clinical trial in Europe chiefly in treatment of the leukemias and of multiple myeloma.

Chemical modification of VLB and vincristine has centered around hydrolysis of the 4-acetoxy group to yield 4-desacetyl VLB (DAVLB) or 4-desacetylvincristine (DAVCR) followed by reesterification with other acyl and amino-acyl groups—see U.S. Pat. Nos. 3,392,173 and 3,387,001—, and replacement of the C-3 ester function by an amide function—see Belgian Pat. No. 837,390. One of the former 4-acyl derivatives, the 4-N,N-dimethylglycine ester underwent a brief clinical trial and one of the latter, vindesine, (4-desacetyl VLB C-3 carboxamide) is currently being tested clinically against a variety of neoplasms.

Other chemical modification of the VLB molecule such as hydrolysis and decarboxylation of the C-18' carbomethoxy group has resulted in a loss of anti-cancer activity as has the formation of N-oxides; i.e., pleurosine (leurosine N-oxide). Oxidative attack on VLB under temperatures higher than −60° C. has resulted in the formation of a chemotherapeutically inactive compound, vinamidine, represented by the following formula:

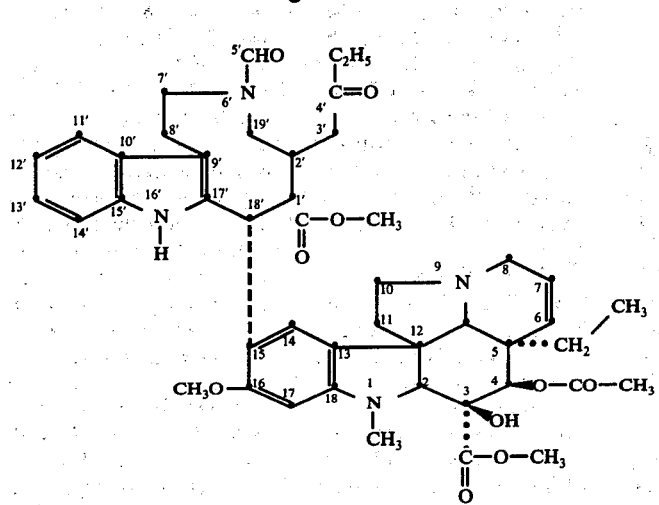

Vinamidine has been encountered in alkaloidal fractions from Vinca rosea leaves—see Tafur et al. J. Pharm. Sci., 64, 1953 (1975)—but the structure assigned therein (II on page 1956) is now believed to be incorrect and the above structure more closely represents the NMR, IR, and molecular spectral data obtained from physiochemical studies of the compound. Vinamidine may arise from oxidative attack on VLB in which a vicinal dihydroxy derivative is formed which, upon further oxidation, splits between the hydroxyl(4',5'-bond) to yield a ring-opened derivative such as II above.

Kutney, et al. in Heterocycles, 4, 1377 (1976), report the preparation of a leurosine lactam called by the authors 19'-oxoleurosine, formed by the action of iodine on leurosine and also refer to the preparation of 5'-oxoleurosine by the oxygenation of 3',4'-dehydrovinblastine or of leurosine.

It is an object of this invention to prepare stable 5'-oxygenated derivatives of leurosine and leuroformine as well as other novel 5'-derivatives thereof.

SUMMARY OF THE INVENTION

In fulfillment of the above and other objects, this invention provides dimeric indole-dihydroindole alkaloids of the formula:

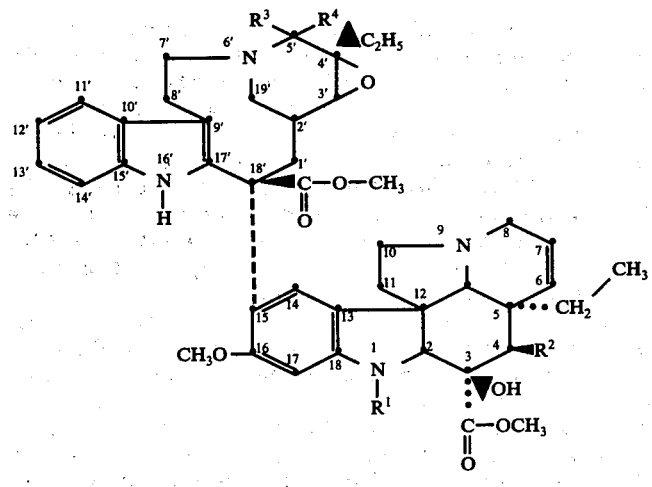

wherein $R^1$ is $CH_3$ or CHO, $R^2$ is OH or acetoxy, and, when taken singly, one of $R^3$ and $R^4$ is hydrogen and the other is OH or $CH_2COCH_3$ and, when taken together $R^3$ and $R^4$ form an oxygen atom.

Also included within the scope of this invention are the pharmaceutically-acceptable acid addition salts of the above alkaloidal bases including salts derived from inorganic acids such as: hydrochloric acid, nitric acid, phosphoric acid, sulfuric acid, hydrobromic acid, hydriodic acid, nitrous acid, phosphorus acid and the like, as well as salts of organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include the sulfate pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

In the above formula, when $R^1$ is $CH_3$ and $R^2$ is acetoxy, the compounds are denominated as 5' derivatives of leurosine; when $R^1$ is $CH_3$ and $R^2$ is hydroxy, of 4-desacetylleurosine; when $R^1$ is CHO and $R^2$ is acetoxy, of leuroformine; and, when $R^1$ is CHO and $R^2$ is hydroxy, of 4-desacetylleuroformine.

In the above discussion and in Formula III, the oxygenated derivatives of leurosine and leuroformine of this invention are assigned to C-5' rather than C-19'. The assignment of the hydroxyl and oxo groups to C-5' is based upon the best interpretation of the physiochemical data available, but further data or more sophisticated interpretation of available data might lead to the conclusion that the compounds of this invention are C-19' derivatives. It is intended herein to claim hydroxyleurosine, oxoleurosine, hydroxyformylleurosine, etc. prepared by the methods outlined herein and having the physiochemical properties disclosed therefor.

The compounds of this invention are prepared by oxidizing leurosine. For example, leurosine on remaining in contact with air at ambient temperatures will form 5'-hydroxyleurosine. Likewise, bubbling oxygen through a solution of leurosine results in the formation of 5'-hydroxyleurosine. Oxidizing agents such as manganese dioxide, chromium trioxide, pyridinium chlorochromate and the like at ambient temperature or below in suitable solvents also react with leurosine to yield 5'-hydroxyleurosine. Further oxidation with the same reagents, either by prolonging contact times or by using more stringent reaction conditions, converts the 5'-hydroxyl group to a 5'-carbonyl or yields the 5'-oxo derivative directly from leurosine or leuroformine. Reaction of the 5'-hydroxyl derivative with acetone under strongly acidic conditions results in the formation of 5'-acetonylleurosine or 5'-acetonylleuroformine.

Compounds according to III above wherein $R^1$ is formyl (CHO) can be prepared either by direct oxidative attack at C-5', as outlined above on leurosine, on leuroformine or in the instance of 5'-hydroxyleuroformine by low-temperature chromic acid oxidation of 5'-hydroxyleurosine. Compounds according to III above in which $R^2$ is OH and $R^1$ is $CH_3$ or CHO are prepared by mild alkaline hydrolysis of 5'-hydroxy or 5'-oxo leurosine or leuroformine etc., to yield compounds such as 5'-hydroxy-4-desacetylleuroformine, 5'-acetonyl-4-desacetylleurosine, 5'-oxo-4-desacetylleurosine and the like.

Although compounds in which the piperidine ring in the velbanamine moiety has been broken open, as in vinamidine, have been isolated from various of the above oxidation reactions as by-products, the chief product of the initial oxidation has an intact velbanamine ring system as shown by the reduction of 5'-hydroxyleurosine or 5'-hydroxyleuroformine with a metal hydride reducing agent such as sodium cyanoborohydride to regenerate leurosine or leuroformine. This reduction reaction is most important as an alternate method of preparing leuroformine from 5'-hydroxyleurosine by oxidation to 5'-hydroxyleuroformine followed by hydride reduction and as a method of increasing the availabiltiy of leurosine by reducing 5'-hydroxyleurosine to leurosine which latter compound can, of course, be oxidized to leuroformine. Thus, the compounds of this invention in which $R^3$ and $R^4$ represent hydroxy are useful intermediates for giving increased yields of leurosine or for providing a novel synthesis of leuroformine.

This invention is further illustrated by the following specific examples:

EXAMPLE I

Isolation of 5'-Hydroxyleurosine

Ten grams of leurosine obtained from leaves of Vinca rosea were allowed to stand in contact with air for about 2 years. The leurosine was then dissolved in methylene dichloride and placed on a chromatographic column consisting of a cylinder 66 × 3.8 cm. packed with 300 g. of silica gel (Woelm activity I). The column material was slurried in a 3:1 methylene dichloride/ethyl acetate solvent mixture containing 2 percent ethanol. The chromatogram was developed with the same solvent mixture (2.4 liters) followed by 3:1 methylene dichloride/ethyl acetate containing 4 percent ethanol (0.5 liters), 6 percent ethanol (0.5 liters), 8 percent ethanol (0.5 liters), 10 percent ethanol (0.5 liters), and 12 percent ethanol (0.5 liters). The first two fractions, amounting to 1 liter of eluant yielded nothing, but the next six fractions (Fractions 3-8) (each of 0.2 liter) contained a high $R_f$ material. These fractions were combined and the solvent removed there from by evaporation in vacuo, yielding 2.6 g. of a white solid residue. The residue by TLC was substantially one-spot material, indicating the presence of only a single compound ($R_f$ = 0.73). A white solid material obtained by chromatography proved to be 5'-hydroxyleurosine.

EXAMPLE 2

Preparation of 5'-Hydroxyleurosine by Oxidation of Leurosine 200 mg. of leurosine purified by the procedure of Example 1 and kept out of contact with oxygen were dissolved in 7 ml. of methylene dichloride. 1 g. of activated manganese dioxide was added and the reaction mixture stirred magnetically in a stoppered flask at ambient temperature. After 1.4 hours, TLC using a 1:1:1 methylene dichloride/ethyl acetate/ methanol solvent mixture showed two spots, a high $R_f$ spot at 0.79 and a leurosine spot at 0.63. At 2.4 hours, TLC showed the oxidation reaction to be substantially complete (no leurosine remaining) but stirring was continued for an additional 0.7 hours. At this point, the reaction mixture was filtered through Celite to remove inorganic salts and the Celite was washed with methylene dichloride. Concentration of the filtrate yielded 155 mg. of a light gray-brown solid. TLC indicaed that the product was identical to 5'-hydroxyleurosine previously obtained. 5'-Hydroxyleurosine has the following physical characteristics:

pmr at 220 $MH_z$ $\delta$ $_{TMS}^{CDCl_3}$ 9.66 (brs, 1H, C(3)—OH), 8.01 (br s, 1H, indole N-H), 7.47-7.56 (m, 1H, C(11')—H), 7.07-7.23 (m, 3H, C(12'-14')—H), 6.65 (s, 1H, C(14)—H), 6.15 (s, 1H, C(17)—H), 5.87 (brdd, J=4 and 10 Hz, 1H, C(7)—H), 5.49 (s, 1H, C(4)—H), 5.33 (brd, 1H, C(6)—H), 4.58-4.81 (m, 1H, C(5')—H), 3.82 and 3.83 (2s, 6H, C(24,25)—3H), 3.75 (s, 1H, C(2)—H), 3.63 (s, 3H, C(18')—$CO_2CH_3$), 2.75 (s, 3H, N—$CH_3$), 2.67 (s, 1H, C(19)—H), 2.13 (s, 3H, C(4)—$OCOCH_3$), 0.84 and 0.97 (2t, J=7Hz, 6H, C(21,21')—3H).

ultraviolet spectrum: $\lambda_{max}^{EtOH}$ = 216 ($\epsilon^o$ = 4.33 × $10^4$), 262, 290, 298 nm.

infrared spectrum: $\mu$ ($CHCl_3$) = 3450, 1734, 1230 $cm^{-1}$.

titration: pK$_a$' (66% DMF) at 6.80, 4.84.

mass spectrum: peaks at (no M+ at 824) 822, 808, 807, 806, 788, 757, 493, 282, 135.

EXAMPLE 3

Preparation of 5'-Oxoleurosine

A reaction mixture was prepared containing 100 mg. of leurosine purified as in Example 1, 500 mg. of activated manganese dioxide and 3 ml. of methylene dichloride. The reaction mixture was stirred in a stoppered flask at ambient temperature for 15 hours. TLC using a 1:1:1 methylene dichloride/ethyl acetate/methanol solvent mixture indicated that a small amount of leurosine remained, but that a second component was apparently present. This component was detected in a TLC procedure employing a 20:1:1:1 ether/toluene/diethylamine/methanol solvent mixture as a material moving slightly more slowly than 5'-hydroxyleurosine. Stirring of the reaction mixture was continued and at 17 hours, an additional 0.5 g. of manganese dioxide in 2 ml. of methylene dichloride were added. At 23 hours, TLC indicated that no leurosine was present and that little or no 5'-hydroxyleurosine remained. The reaction was interrupted at 24 hours and the reaction mixture filtered through Celite. The Celite was washed with methylene dichloride and the filtrate evaporated to yield 56.4 mg. of 5'-oxoleurosine formed in the above reaction. The residue was washed through 1 g. of Woelm (activity I) silica gel using a 1:1:1 methylene dichloride/ethyl acetate/methanol solvent mixture to remove dark insoluble material. The purified product was concentrated three times from chloroform and, as purified, had the following physical characteristics:

pmr 100 mHz: δ $_{TMS}^{CDCL_3}$ 9.66 (brs, 1H, C(3)—OH), 8.03 (brs, 1H, indole N–H), 7.45–7.61 (m, 1H, C(11')—H), 7.00–7.25 (m, 3H, C(12'–14')—H), 6.61 (s, 1H, C(14)—H), 6.15 (s, 1H, C(17)—H), 5.86 (brdd, J=10 and 4 Hz, 1H, C(7)—H, 5.48 (s, 1H, C(4)—H), 5.30 (brd, J=10Hz, 1H, C(6)—H), 4.60-4.90 (m, 1H, C(2')—H), 3.80 and 3.83 (2s, 6H, C(24,25)—3H), 3.79 (s, 1H, C(2)—H), 3.60 (s, 3H, C(18')—CO$_2$CH$_3$), 2.74 (s, 3H, N—CH$_3$), 2.65 (s, 1H, C(19)—H), 2.10 (s, 3H, C(4)—OCOCH$_3$), 0.70–1.10 (m, 6H, C(21,21')—3H).

infrared spectrum: μ (CHCl$_3$) = 3450, 1730, 1634, 1608, 1230 cm$^{-1}$.

titration: pK$_a$' (66% DMF) at 5.20.

EXAMPLE 4

Conversion of 5'-Hydroxyleurosine to Leurosine

In order to partially substantiate the structure attributed to the leurosine oxidation product of Examples 1 and 2, 200 mg. of 5'-hydroxyleurosine were treated with 50 mg. of sodium cyanoborohydride in THF. 0.75 ml. of 1N aqueous hydrochloric acid were added to dissolve the reactants. Stirring of the reaction mixture was continued for 1.2 days. Thin-layer chromatography using 1:1 methylene dichloride/ethyl acetate solvent containing 5 percent methanol indicated the presence of leurosine.

A similar reaction carried out on a larger scale (10 g. of 5'-hydroxyleurosine) yielded 7.5 g. of leurosine containing a trace of 5'-oxoleurosine as determined by thin-layer chromatography. The same reaction can be carried out on 5'-hydroxy-1-formyl-1-desmethylleurosine (5'-hydroxyleuroformine) to yield leuroformine itself.

EXAMPLE 5

Preparation of 5'-Acetonylleurosine 100 mg. of 5'-hydroxyleurosine were mixed with 5 ml. of acetone. 0.3 ml. of 1.0 N aqueous hydrochloric acid were added. During the addition, the 5'-hydroxyleurosine dissolved. The reaction mixture was stirred at ambient temperature for 1.75 hours. Thin-layer chromatography using a 4:2:1 benzene/chloroform/methanol solvent mixture indicated a new product with only a trace of 5'-hydroxyleurosine remaining. The reaction was terminated at 2.3 hours by dilution with methylene dichloride, water, and 1.0 N aqueous sodium hydroxide to a pH of about 11–12. The organic phase was separated and the aqueous phase extracted twice with methylene dichloride. The three organic layers were combined, washed twice with water, and dried. Evaporation of the methylene dichloride in vacuo yielded 104 mg. of 5'-acetonylleurosine similar in physical properties to the product, 5'-acetonylvincristine, disclosed in the copending application of Barnett, et al., Ser. No. 801,132 filed May 27, 1977.

EXAMPLE 6

Preparation of 5'-Hydroxyleuroformine

A solution was prepared from 2.0 g. of 5'-hydroxyleurosine, 20 ml. of methylene dichloride and 250 ml. of acetone. The mixture was cooled in a dry-ice-chloroform bath to about −61° C. 7.5 ml. of glacial acetic acid were added followed by the dropwise addition of a solution containing 2 g. of chromium trioxide in 4 ml. of water and 20 ml. of glacial acetic acid. The resulting mixture was stirred at −61° C. for about 4 hours, after which time 14 N ammonium hydroxide and water were added. The alkaline aqueous layer was extracted three times with methylene dichloride; the methylene dichloride extracts were combined, washed once with water, and dried. Evaporation of the solvent in vacuo yielded a residue comprising 5'hydroxyleuroformine formed in the above reaction. The residue was purified by chromatography over silica using a 1:1:1 methylene dichloride/methanol/ethyl acetate solvent mixture as the eluant. Fractions shown to contain 5°-hydroxyleuroformine by thin-layer chromatography were combined and yielded 950 mg. of material having the following physical characteristics:

Infrared spectrum (chloroform): peaks at 3700, 3500, 1740, and 1690 cm$^{-1}$.

Mass spectrum: (m/e) 822 molecular ion −16), 369, 353, 168.

titration: (66% aqueous DMF) pK$_a$ = 4.63, 6.83.

The above compound can also be be prepared by oxidation of leuroformine with manganese dioxide according to the procedure of Example 2. Following the procedure of Example 4, 5'-hydroxyleuroformine can be reduced to leuroformine by the action of sodium cyanoborohydride in a suitable solvent such as THF. Other metal hydrides of equivalent reducing power may also be used in place of sodium cyanoborohydride.

EXAMPLE 7

Preparation of Salts

Salts, including salts with inorganic anions such as chloride, bromide, phosphate, nitrate and the like as well as salts with organic anoins such as acetate, chloroacetate, trichloroacetate, benzoate, alkyl or aryl sulfonates and the like, are prepared from the amine bases of this invention as follows, using the sulfate salt for exemplary purposes only. 5'-Hydroxyleurosine was dissolved in methanol and the pH adjusted to 2.9 with 1 percent sulfuric acid. Evaporation of the resulting mixture in vacuo yielded 5'-hydroxyleurosine sulfate as an amorphous powder. Other salts can be prepared in analogous fashion.

The compounds of this invention are active against transplanted tumors in mice in vivo and induce metaphase arrest in Chinese hamster ovary cells maintained in tissue culture in a procedure adapted from that of Siminoff, Applied Microbiology, 9, 66—72 (1961).

In demonstrating activity of the drugs of this invention against transplanted tumors in mice, a protocol was used which involved the administration of the drug, usually by the intraperitoneal route, at a given dose level for 3-10 days after innoculation with the tumor. 5'-Hydroxyleurosine has demonstrated activity in such a test against CA755 adenocarcinoma at 4.0 and 6.0 mg/kg. administered on ten successive days. 5'-Oxoleurosine demonstrated marginal activity against the same tumor at the 4-5 mg/kg. level.

In utilizing the novel compounds of this invention as anti-tumor agents in mannals, the parenteral route of administration is conveniently employed. With parenteral administration, the intravenous route is preferred although with smaller mammals such as mice the intraperitoneal route may be used. For parenteral administration, isotonic solutions are employed containing 1–10 mg./ml. of a salt of the alkaloidal base formula III. The compounds are administered at a rate of from 0.01 to 2 mg./kg. and preferably from 0.1 to 1 mg./kg. of mammalian body weight once or twice a week or every two weeks depending on both the activity and the toxicity of the drug. An alternative method of arriving at a therapeutic dose is based on body — surface area with a dose in the range 0.1 to 10 mg./meter squared of mammalain body surface every 7 or 14 days.

We claim:

1. A dimeric indole-dihydroindole alkaloid of the formula:

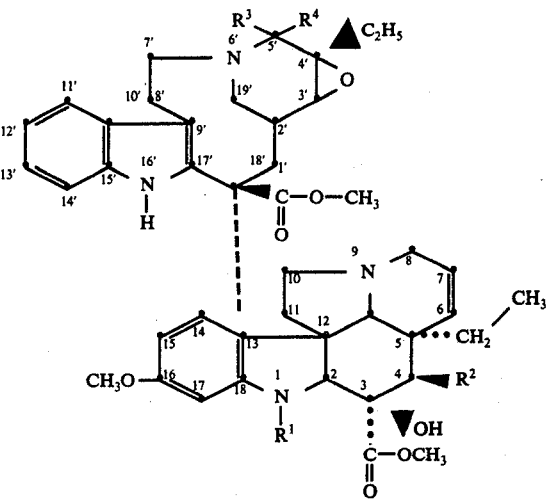

wherein $R^1$ is $CH_3$ or CHO, $R^2$ is OH or acetoxy, and, when taken singly, one of $R^3$ and $R^4$ is hydrogen and the other is OH or $CH_2COCH_3$ and, when taken together, $R^3$ and $R^4$ form an oxygen atom, and pharmaceutically-acceptable acid addition salts thereof.

2. A compound according to claim 1 wherein $R^1$ is $CH_3$, $R^2$ is acetoxy and one of $R^3$ and $R^4$ is H and the other OH, said compound being 5'-hydroxyleurosine.

3. A compound according to claim 1 wherein $R^1$ is CHO, $R^2$ is acetoxy and one of $R^3$ and $R^4$ is H and the other OH, said compound being 5'-hydroxyleuroformine.

4. A compound according to claim 1 wherein $R^1$ is $CH_3$, $R^2$ is acetoxy and $R^3$ and $R^4$ taken together are oxygen, said compound being 5'-oxoleurosine.

5. 5'-Hydroxyleurosine having the following physical characteristics:

pmr at 220 MH$_z$ $\delta_{TMS}^{CDCl_3}$ 9.66 (br s, 1H, C(3)—OH), 8.01 (br s, 1H, indole N—H), 7.47-7.56 (m, 1H, C(11')—H), 7.07-7.23 (m, 3H, C(12'-14')—H), 6.65 (s, 1H, C(14)—H), 6.15 (s, 1H, C(17)—H), 5.87 (brdd, J=4 and 10 Hz, 1H, C(7)—H), 5.49 (s, 1H, C(4)—H), 5.33 (brd, 1H, C(6)—H), 4.58-4.81 (m, 1H, C(5')—H), 3.82 and 3.83 (2s, 6H, C(24,25)—3H), 3.75 (s, 1H, C(2)—H), 3.63 (s, 3H, C(18')—CO$_2$CH$_3$), 2.75 (s, 3H, N—CH$_3$), 2.67 (s, 1H, C(19)—H), 2.13 (s, 3H, C(4)—OCOCH$_3$), 0.84 and 0.97 (2t, J=7Hz, 6H, C(21,21')—3H).

ultraviolet spectrum: $\lambda_{max}^{EtOH}$ = 216 ($\epsilon^\circ$ = 4.33 × 10$^4$), 262, 290, 298 nm.

infrared spectrum: $\mu$ (CHCl$_3$) = 3450, 1734, 1230 cm$^{-1}$.

titration: pK$_a'$ (66% aqueous DMF) at 6.80, 4.84.

mass spectrum: peaks at 822, 808, 807, 806, 788, 757, 493, 282, 135.

* * * * *